US007962211B2

(12) United States Patent
Torgerson et al.

(10) Patent No.: US 7,962,211 B2
(45) Date of Patent: Jun. 14, 2011

(54) ANTENNA FOR AN EXTERNAL POWER SOURCE FOR AN IMPLANTABLE MEDICAL DEVICE, SYSTEM AND METHOD

(75) Inventors: Nathan A. Torgerson, Andover, MN (US); John E. Kast, Hugo, MN (US); Kevin J. Kelly, Shoreview, MN (US); Todd P. Goblish, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 1057 days.

(21) Appl. No.: 11/414,151

(22) Filed: Apr. 28, 2006

(65) Prior Publication Data

US 2007/0255349 A1  Nov. 1, 2007

(51) Int. Cl.
*A61N 1/378* (2006.01)
*A61N 1/40* (2006.01)

(52) U.S. Cl. ............. 607/33; 607/61; 607/75; 607/65; 607/155

(58) Field of Classification Search ............ 607/33, 607/60, 61, 63, 65, 75, 155
See application file for complete search history.

(56) References Cited

U.S. PATENT DOCUMENTS

| 5,279,292 A * | 1/1994 | Baumann et al. ............ 607/137 |
| 5,411,537 A | 5/1995 | Munshi et al. |
| 5,545,191 A * | 8/1996 | Mann et al. ............ 607/57 |
| 5,690,693 A | 11/1997 | Wang et al. |
| 5,733,313 A | 3/1998 | Barreras et al. |
| 6,308,101 B1 | 10/2001 | Faltys et al. |
| 6,324,430 B1 | 11/2001 | Zarinetchi et al. |
| 6,477,425 B1 | 11/2002 | Nowick et al. |
| 6,505,077 B1 | 1/2003 | Kast et al. |
| 6,516,227 B1 | 2/2003 | Meadows et al. |
| 7,512,443 B2 * | 3/2009 | Phillips et al. ............ 607/61 |
| 2005/0075700 A1 | 4/2005 | Schommer et al. |
| 2006/0030905 A1 | 2/2006 | Medina |

FOREIGN PATENT DOCUMENTS

| EP | 1 048 324 A2 | 11/2000 |
| EP | 1 048 324 A3 | 10/2002 |
| GB | 2 239 802 A | 7/1991 |
| WO | WO 01/83029 A1 | 11/2001 |
| WO | WO 01/85250 A | 11/2001 |
| WO | WO 01/97908 A2 | 12/2001 |
| WO | WO 01/97908 A3 | 12/2001 |

OTHER PUBLICATIONS

International Search Report for PCT/US2005/001770.
International Search Report forPCT/US2007/002029.

* cited by examiner

*Primary Examiner* — Carl H Layno
*Assistant Examiner* — Natasha N Patel
(74) *Attorney, Agent, or Firm* — IPLM Group, P.A.

(57) ABSTRACT

System, method and antenna for an external power source for an implantable medical device having therapeutic componentry and a secondary coil operatively coupled to the therapeutic componentry. A housing has a first surface adapted to be placed closest to the secondary coil of the implantable medical device. A primary coil is operatively coupled to the external power and is capable of inductively energizing the secondary coil, the primary coil being wound forming generally concentric loops having an axis. The housing has a protrusion extending from the first surface.

27 Claims, 7 Drawing Sheets

ANTENNA FOR AN EXTERNAL POWER SOURCE FOR AN IMPLANTABLE MEDICAL DEVICE, SYSTEM AND METHOD

FIELD

The present invention relates generally to transcutaneous energy transfer for an implantable medical device and, more particularly, to an antenna for an external power source for such transcutaneous energy transfer.

BACKGROUND

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators and cochlear implants. Of course, it is recognized that other implantable medical devices are envisioned which utilize energy delivered or transferred from an external device.

A common element in all of these implantable medical devices is the need for electrical power in the implanted medical device. The implanted medical device requires electrical power to perform its therapeutic function whether it is driving an electrical infusion pump, providing an electrical neurostimulation pulse or providing an electrical cardiac stimulation pulse. This electrical power is derived from a power source.

Typically, a power source for an implantable medical device can take one of two forms. The first form utilizes an external power source that transcutaneously delivers energy via wires or radio frequency energy. Having electrical wires which perforate the skin is disadvantageous due, in part, to the risk of infection. Further, continuously coupling patients to an external power for therapy is, at least, a large inconvenience. The second form utilizes single cell batteries as the source of energy of the implantable medical device. This can be effective for low power applications, such as pacing devices. However, such single cell batteries usually do not supply the lasting power required to perform new therapies in newer implantable medical devices. In some cases, such as an implantable artificial heart, a single cell battery might last the patient only a few hours. In other, less extreme cases, a single cell unit might expel all or nearly all of its energy in less than a year. This is not desirable due to the need to explant and re-implant the implantable medical device or a portion of the device. One solution is for electrical power to be transcutaneously transferred through the use of inductive coupling. Such electrical power or energy can optionally be stored in a rechargeable battery. In this form, an internal power source, such as a battery, can be used for direct electrical power to the implanted medical device. When the battery has expended, or nearly expended, its capacity, the battery can be recharged transcutaneously, via inductive coupling from an external power source temporarily positioned on the surface of the skin.

Several systems and methods have been used for transcutaneously inductively recharging a rechargeable used in an implantable medical device. Some examples of systems and method used for transcutaneously inductively charging or recharging an implantable medical device include U.S. Pat. No. 5,411,537, Munshi et al, Rechargeable Biomedical Battery Powered Devices With Recharging and Control System Therefor, (Intermedics, Inc.); U.S. Pat. No. 5,690,693, Wang et al, Transcutaneous Energy Transmission Circuit For Implantable Medical Device, (Sulzer Intermedics Inc.); U.S. Pat. No. 5,733,313, Barreras, Sr., FR Coupled Implantable Medical Device With Rechargeable Back-Up Power Source, (Exonix Corporation); U.S. Pat. No. 6,308,101, Faltys et al, Fully Implantable Cochlear Implant System, (Advanced Bionics Corporation); U.S. Pat. No. 6,324,430, Zarinetchi et al, Magnetic Shield For Primary Coil of Transcutaneous Energy Transfer Device, (Abiomed, Inc.); U.S. Pat. No. 6,516,227, Meadows et al, Rechargeable Spinal Cord Stimulator System, (Advanced Bionics Corporation); U.S. Pat. No. 6,505,077, Kast et al, Implantable Medical Device With External Recharging Coil Electrical Connection, (Medtronic, Inc.); European Patent Application 1,048,324, Schallhorn, Medical Li+ Rechargeable Powered Implantable Stimulator, (Medtronic, Inc.); PCT Patent Application No. WO 01/83029 A1, Torgerson et al, Battery Recharge Management For an Implantable Medical Device, (Medtronic, Inc.); and PCT Patent Application No. WO 01/97908 A2, Jimenez et al, An Implantable Medical Device With Recharging Coil Magnetic Shield, (Medtronic, Inc.).

U.S. Patent Application Publication US 2005/0075700A1 (U.S. patent application Ser. No. 10/837,506, Schommer et al, External Power Source For An Implantable Medical Device Having An Adjustable Magnetic core and System and Method Related Therefore, filed Apr. 30, 2004), discloses an external power source, and system and method using such external power source, for an implantable medical device having therapeutic componentry and a secondary coil operatively coupled to the therapeutic componentry. A primary coil is capable of inductively energizing the secondary coil when externally placed in proximity of the secondary coil. A repositionable magnetic core associated with the primary coil is capable of being repositioned by a user of the external power source. An indicator is capable of providing the user with information relative to coupling between the primary coil and the secondary coil as a function of repositioning of the repositionable magnetic core.

Transcutaneous energy transfer through the use of inductive coupling involves the placement of two coils positioned in close proximity to each other on opposite sides of the cutaneous boundary. The internal coil, or secondary coil, is part of or otherwise electrically associated with the implanted medical device. The external coil, or primary coil, is associated with the external power source or external charger, or recharger. The primary coil is driven with an alternating current. A current is induced in the secondary coil through inductive coupling. This current can then be used to power the implanted medical device or to charge, or recharge, an internal power source, or a combination of the two.

For implanted medical devices, the efficiency at which energy is transcutaneously transferred is crucial. First, the inductive coupling, while inductively inducing a current in the secondary coil, also has a tendency to heat surrounding components and tissue. The amount of heating of surrounding tissue, if excessive, can be deleterious. Since heating of surrounding tissue is limited, so also is the amount of energy transfer which can be accomplished per unit time. The higher the efficiency of energy transfer, the more energy can be transferred while at the same time limiting the heating of surrounding components and tissue. Second, it is desirable to limit the amount of time required to achieve a desired charge, or recharge, of an internal power source. While charging, or recharging, is occurring the patient necessarily has an external encumbrance attached to their body. This attachment may impair the patient's mobility and limit the patient's comfort. The higher the efficiency of the energy transfer system, the faster the desired charging, or recharging, can be accomplished limiting the inconvenience to the patient. Third, amount of charging, or recharging, can be limited by the amount of time required for charging, or recharging. Since the patient is typically inconvenienced during such charging, or recharging, there is a practical limit on the amount of time during which charging, or recharging, should occur. Hence, the size of the internal power source can be effectively limited by the amount of energy which can be transferred within the amount of charging time. The higher the efficiency of the energy transfer system, the greater amount of energy which can be transferred and, hence, the greater the practical size of the internal power source. This allows the use of implantable medical devices having higher power use requirements and providing greater therapeutic advantage to the patient and/or extends the time between charging effectively increasing patient comfort.

The efficiency of transcutaneous inductive energy transfer is directly related to the accuracy of positioning of the external, primary coil, to the internal, secondary coil. The two coils should be as close to each other as possible. Of course, since the position of the secondary coil is fixed following implantation, the closer that the primary coil can be positioned to the skin surface the better. The two coils should also be laterally aligned as close as possible. This alignment is typically accomplished by the patient by the attachment of the external power source/charger at the commencement of the charging process or when otherwise transferring power. It is often cumbersome and difficult for the patient, who typically is not a medical professional, to most accurately position the primary coil in the proper location. The lateral alignment is typically done tactilely by the patient. A typical implanted medical device is implanted close enough to the skin that the skin of the patient has a small protuberance at the site of implantation. This can be felt by the patient and can be used as a guide to position the external coil. However, this problem can be exacerbated because the lateral position of the secondary coil is not always laterally centered with the external protuberance providing the patient with tactile lateral location information.

Even if the primary coil is properly placed at the initiation of energy transfer or of the charging process, energy transfer and/or charging can continue over a signification period of time. During this time, it is usually impracticable for the patient to remain absolutely immobile. Charging can typically occur over several, perhaps many, hours. It is desirable for the patient to be able to continue with as many normal activities as possible. For example, since charging often is accomplished at night, it is desirable that the primary coil not move during normal sleep activities of the patient. As the patient may move during energy transfer or during charging, motions and activities of the patient may cause the primary coil to move with respect to the secondary coil. If this should happen, the efficiency of energy transfer is not optimum which limits the rate at which energy can be transferred and resulting in an increase in charging time, if the system utilizes charging, or a decrease in the amount of energy available to the implanted medical device, if direct energy transfer is utilized.

It also can be important to secure the primary coil in the proper location once the proper has been located by the patient.

Prior art implantable medical devices, external power sources, systems and methods have not always provided the best possible benefit leading to efficiency of energy transfer and patient comfort.

SUMMARY

A bump, or protrusion, on the surface of an external antenna closest to a secondary coil of an implanted medical device allows a greater efficiency of energy transfer as compared with external antennas having a flat, or relatively flat, surface closest to the implanted medical device.

When the external antenna having such protrusion is positioned in charging position against the surface of the skin, the protrusion pushes skin away from the primary coil and allows the primary coil to get closer to the secondary coil in a direction orthogonal to the surface of the skin increasing energy transfer efficiency.

Increased efficiency of energy transfer can result in a reduction in heat build-up during transcutaneous energy transfer and/or shorten the time required to transfer a given amount of energy, e.g., reducing the time required to charge or recharge an implanted medical device.

In an embodiment, the present invention provides an antenna for an external power source for an implantable medical device having therapeutic componentry and a secondary coil operatively coupled to the therapeutic componentry. A housing has a first surface adapted to be placed closest to the secondary coil of the implantable medical device. A primary coil is operatively coupled to the external power and is capable of inductively energizing the secondary coil, the primary coil being wound forming generally concentric loops having an axis. The housing has a protrusion extending from the first surface.

In an embodiment, the protrusion is a central protrusion centrally located with respect to the axis of the primary coil.

In an embodiment, the central protrusion comprises a magnetic core.

In an embodiment, a magnetic core is at least partially contained in the central protrusion.

In an embodiment, the housing further has a peripheral protrusion extending from the first surface at least partially surrounding an outer periphery of the primary coil.

In an embodiment, the peripheral protrusion comprises a plurality of bumps, spaced from each other, surrounding the outer periphery of the primary coil and extending from the first surface.

In an embodiment, the peripheral protrusion extends from the first surface approximately one-half centimeter.

In an embodiment, the peripheral protrusion extends from the first surface not greater than central protrusion extends from the first surface.

In an embodiment, the peripheral protrusion extends from the first surface less than the central protrusion extends from the first surface.

In an embodiment, the peripheral protrusion extends from the first surface approximately one-half of the distance the central protrusion extends from the first surface.

In an embodiment, the protrusion is generally aligned with the axis of the primary coil.

In an embodiment, the protrusion has a circular cross-section.

In an embodiment, the protrusion has a round tip.

In an embodiment, at least a portion of the protrusion is conical.

In an embodiment, a diameter of the circular cross-section of the protrusion is not greater than a distance between an inner periphery of the primary coil.

In an embodiment, the protrusion extends from the first surface approximately one-half centimeter.

In an embodiment, an extent of extension of the protrusion from the first surface is adjustable.

In an embodiment, the protrusion comprises a screw having threads adapted to mate with corresponding threads of the housing.

In an embodiment, the present invention provides a system for transcutaneous energy transfer. An implantable medical device has therapeutic componentry and a primary coil capable of inductively energizing the secondary coil when externally placed in proximity of the secondary coil. An antenna has a housing having a first surface adapted to be placed closest to the secondary coil of the implantable medical device. A primary coil is operatively coupled to the external power and is capable of inductively energizing the secondary coil, the primary coil being wound forming generally concentric loops having an axis. The housing has a protrusion extending from the first surface.

In an embodiment, the present invention provides a method of transcutaneous energy transfer to a medical device implanted in a patient having a secondary charging coil using an external power source having a housing containing a primary coil, the housing having a first surface nearest to the secondary coil, the housing having a protrusion extending from the first surface. The primary coil is positioned externally of the patient with respect to the secondary coil. The protrusion is pressed against skin of the patient. Energy is transcutaneously transferred from the primary coil to the secondary coil.

In an embodiment, the protrusion is a central protrusion centrally located with respect to the axis of the primary coil.

In an embodiment, the first surface is further pressed against the skin of the patient.

In an embodiment, the distance of extension of the protrusion is adjusted.

In an embodiment, a peripheral protrusion extending from the first surface at least partially surrounding an outer periphery of the primary coil is pressed against the skin of the patient.

In an embodiment, the peripheral protrusion is a plurality of bumps, spaced from each other, surrounding the outer periphery of the primary coil and extending from the first surface.

In an embodiment, a peripheral protrusion extending from the first surface at least partially surrounding an outer periphery of the primary coil is pressed against the skin of the patient.

In an embodiment, the central protrusion comprises a magnetic core.

In an embodiment, the housing further has a magnetic core carried at least partially in the central protrusion.

In an embodiment, the protrusion, or bump, on the surface of the external antenna closest to the secondary coil can allow a greater efficiency of transcutaneous energy transfer as compared with an external antenna with a flat, or a relatively flat, surface. By adding a protrusion in the z-direction, i.e., the direction orthogonal to a plane defined by the cutaneous boundary, pushes skin away from the primary coil and allows the primary coil to be pressed closer to the secondary coil in the z-direction, thereby increasing transcutaneous energy transfer efficiency. Increased efficiency of energy transfer can result in a reduction in heat build-up during transcutaneous energy transfer and/or in a shortening of the time required to transfer a given amount of energy, e.g., reducing the time required to charge or recharge the implanted medical device.

In an embodiment, a recess developed between peripheral protrusions in the surface of the external antenna closest to the secondary coil can assist with x-y positioning of the external antenna by providing a convenient location assist with the "bump" created by the implanted medical device.

In an embodiment, a magnetic core at least partially located in a central protrusion on the surface of the external antenna closest to the secondary coil can help to additionally focus magnetic flux in the z-direction into the secondary coil.

DRAWINGS

DETAILED DESCRIPTION

Figure 1:
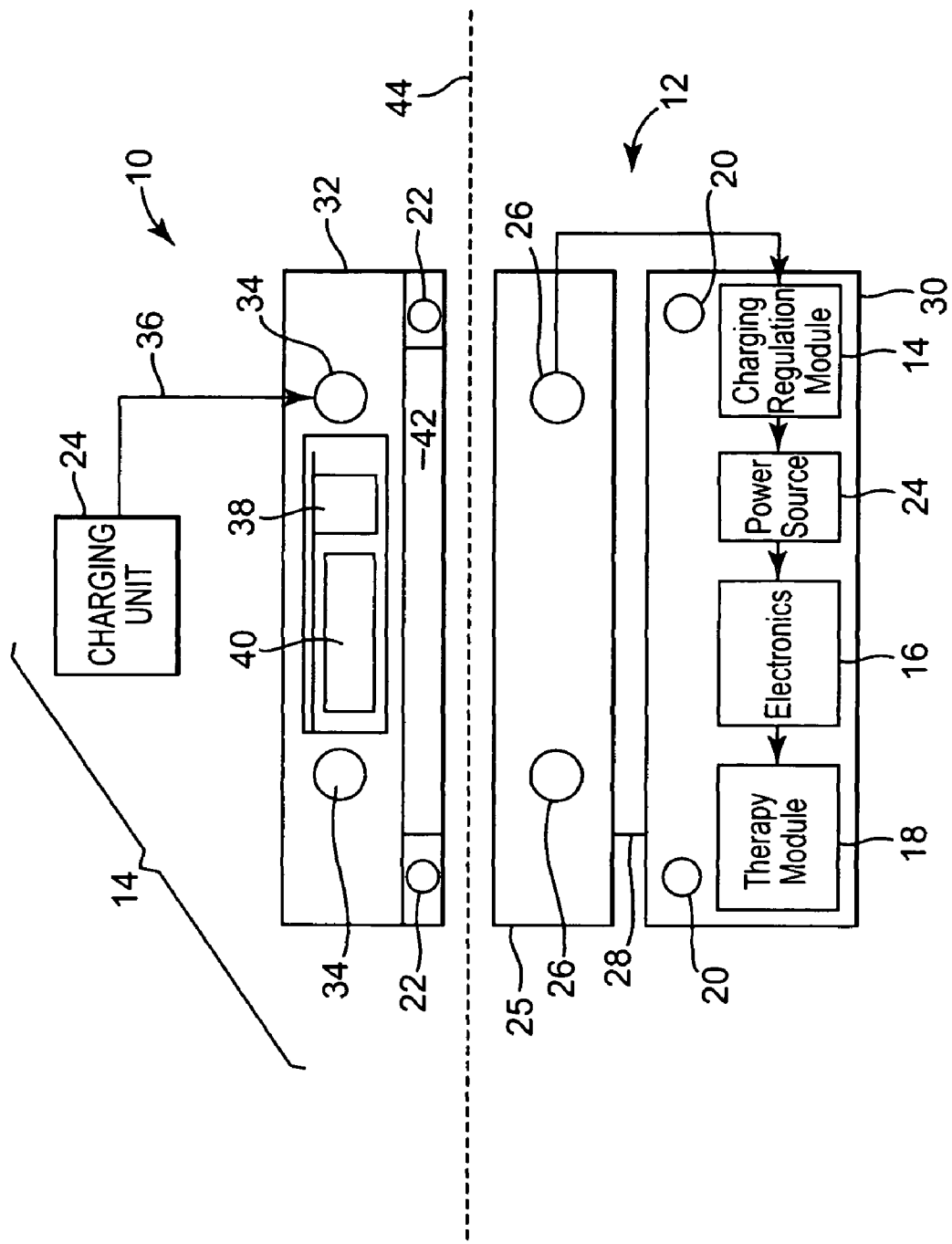
FIG. 1 is a block diagram of a charging system utilizing transcutaneous energy transfer.

FIG. 1 illustrates a system 10 into which an improved external antenna 32 may be utilized. System 10 consists of implantable medical device 12 and external power supply 14.

Implantable medical device 12 is situated under cutaneous boundary 16. Implantable medical device 12 includes charging regulation module 14, electronics module 16 and therapy module 18. Charging regulation and therapy control is conventional. Implantable medical device 12 also has internal telemetry coil 20 configured in conventional manner to communicate through external telemetry coil 22 to an external programming device (not shown), charging unit 24 or other device in a conventional manner in order to both program and control implantable medical device and to externally obtain information from implantable medical device 12 once implantable medical device has been implanted. Internal telemetry coil 20, rectangular in shape with dimensions of 1.85 inches (4.7 centimeters) by 1.89 inches (4.8 centimeters) constructed from 150 turns of 43 AWG wire, is sized to be larger than the diameter of secondary charging coil 26.

Internal antenna 25 contains secondary coil 26, constructed with 182 turns of 30 AWG wire with an inside diameter of 0.72 inches (1.83 centimeters) and an outside diameter of 1.43 inches (3.63 centimeters) with a height of 0.075 inches (0.19 centimeters). Magnetic shield 28 is positioned between secondary charging coil 26 and housing 30 and sized to cover the footprint of secondary charging coil 26.

Internal telemetry coil 20, having a larger diameter than secondary coil 26, is not completely covered by magnetic shield 28 allowing implantable medical device 12 to communicate with the external programming device with internal telemetry coil 20 in spite of the presence of magnetic shield 28.

Rechargeable power source 24 can be charged while implantable medical device 12 is in place in a patient through the use of charging regulation module 14. In a preferred embodiment, charging regulation module 14 consists of charging unit 24 and external antenna 32. Charging unit 24 contains the electronics necessary to drive primary coil 34 with an oscillating current in order to induce current in secondary coil 26 when primary coil 34 is placed in the proximity of secondary coil 26. Charging unit 24 is operatively coupled to primary coil 34 by cable 36. In an alternative embodiment, charging unit 24 and antenna 32 may be combined into a single unit. Antenna 32 may also optionally contain external telemetry coil 22 which may be operatively coupled to charging unit 24 if it is desired to communicate to or from implantable medical device 12 with charging regulation module 14. Alternatively, antenna 32 may optionally contain external telemetry coil 22 which can be operatively coupled to an external programming device, either individually or together with external charging unit 14.

As will be explained in more detail below, repositionable magnetic core 38 can help to focus electromagnetic energy from primary coil 34 to be more closely aligned with secondary coil 26. Also as will be explained in more detail below, energy absorptive material 40 can help to absorb heat build-up in external antenna 32 which will also help allow for a lower temperature in implantable medical device 12 and/or help lower recharge times. Also as will be explained in more detail below, thermally conductive material 42 is positioned covering at least a portion of the surface of external antenna 32 which contacts cutaneous boundary 44 of the patient.

Figure 2:
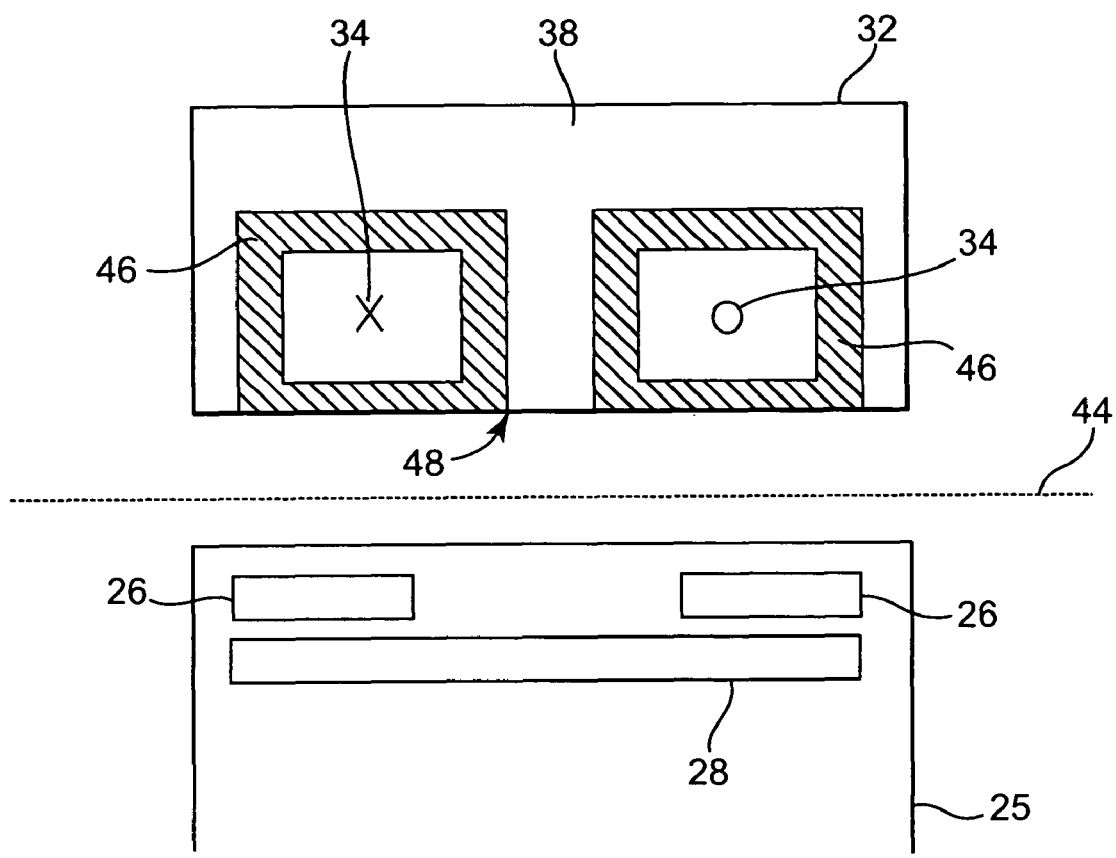
FIG. 2 is a cross-sectional illustration of a close-up view of a variation of a portion of a charging system.

FIG. 2 is a cross-sectional illustration of a close-up view of a variation of a portion of charging system 10. Internal antenna 25 is shown having been implanted below cutaneous boundary 44. Secondary coil 26 is positioned within internal antenna 25 above magnetic shield 28.

External antenna 38 contains primary coil 34 and is positioned in transcutaneous superposition with respect to internal antenna 25. Primary coil 34 is aligned with secondary coil 26 in order to facilitate transcutaneous energy transfer using electromagnetic coupling. Magnetic core 38 helps to focus electromagnetic energy generated by primary coil 34 transcutaneously toward secondary coil 26. In this embodiment, magnetic core 38 extends between windings of primary coil 34. External antenna 32 has a generally planar surface 48 intended to contact cutaneous boundary 44. An edge of magnetic core 38 is coplanar with surface 48 to help promote electromagnetic fields to extend from primary coil 34 and be captured more readily by secondary coil 26. Insulation 46 between magnetic core 38 and primary coil 34, particularly on the side of external antenna 32 facing surface 48, protects magnetic core 38 from collecting heat produced by primary coil 34 and increasing the surface of cutaneous boundary 44.

Figure 3:
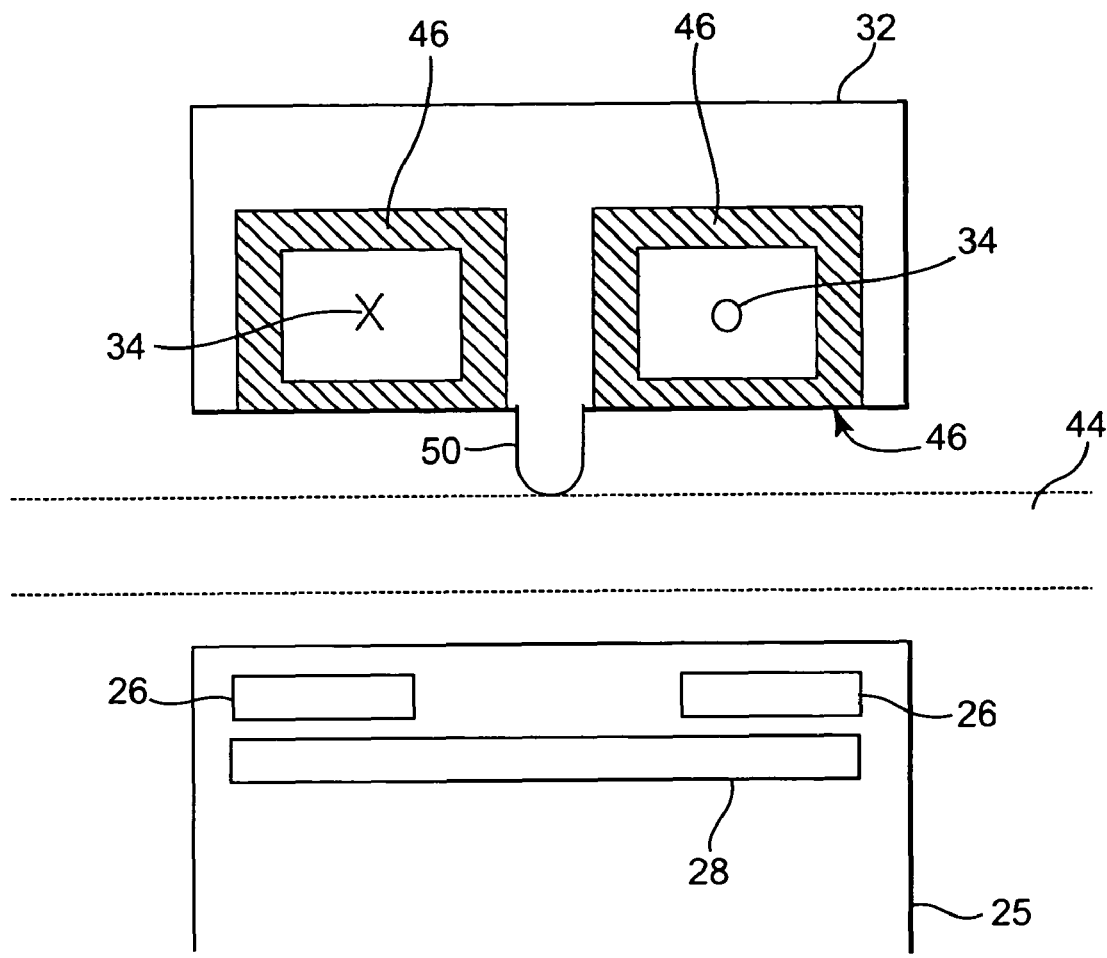
FIG. 3 is a cross-sectional illustration of an embodiment of an external antenna having a central protrusion contacting the cutaneous boundary of the patient.

FIG. 3 illustrates an alternative embodiment of external antenna 32 used in charging system 10. Again, external antenna 38 contains primary coil 34 and is positioned in transcutaneous superposition with respect to internal antenna 25. Primary coil 34 is aligned with secondary coil 26 in order to facilitate transcutaneous energy transfer using electromagnetic coupling. Magnetic core 38 helps to focus electromagnetic energy generated by primary coil 34 transcutaneously toward secondary coil 26. Central protrusion may be aligned with the axis of primary coil 34.

However, external antenna 32 illustrated in FIG. 3 extends magnetic core 38 further toward cutaneous boundary 44 and past surface 48 creating protrusion 50. Central protrusion 50 extends beyond surface 48 creating a noticeable bump on surface 48 contacting cutaneous boundary 44. In an embodiment, central protrusion 50 is circular in cross-section and has a conically shaped end intended to contact cutaneous boundary 44. In an embodiment, central protrusion 50 is approximately 0.5 centimeters in diameter and extends approximately 0.5 centimeters beyond surface 48. The outer diameter of central protrusion 50 may be not greater than, and perhaps less than, the inner diameter of primary coil 34.

Figure 4:
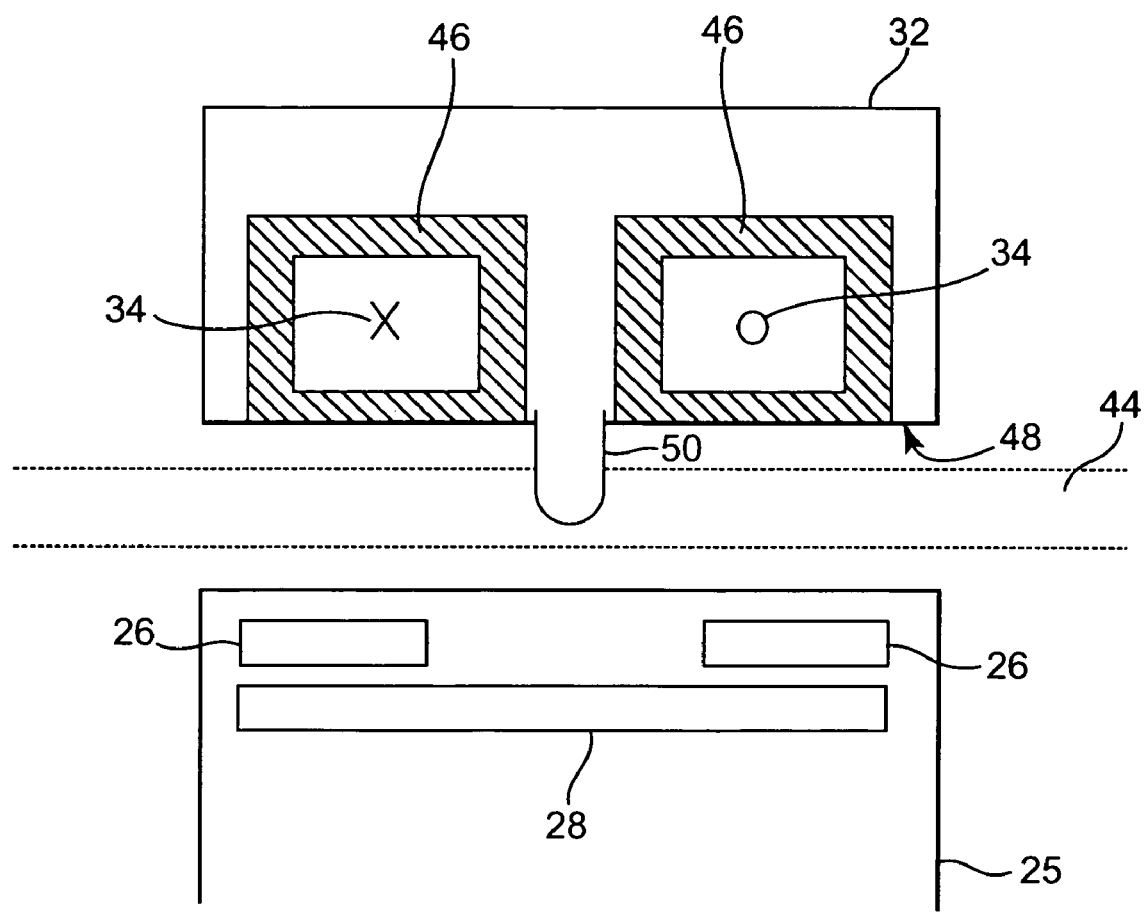
FIG. 4 is a cross-sectional illustration of an embodiment of an external antenna having a central protrusion being pressed against the cutaneous boundary of the patient.

External antenna 32 may be pressed by the user against cutaneous boundary 44 as illustrated in FIG. 4. Central protrusion 50 pushes a portion of cutaneous boundary 44 away from its point of impact allowing external antenna 32, in general, and magnetic core 38, in particular, to come closer to secondary coil 26.

Central protrusion 50 allows primary coil 34 to more efficiently electromagnetically couple with secondary coil 26 by allowing magnetic core 38 to be closer to internal antenna 25 and secondary coil 26. Commonly, an external antenna 32 having a planar surface 48 may be able to come within 1 centimeter of secondary coil 26 of internal antenna 25. However, central protrusion 50 is able to indent cutaneous boundary 44 and reduce the distance, commonly referred as the "air gap distance" between primary coil 34 and secondary coil 26.

Figure 5:
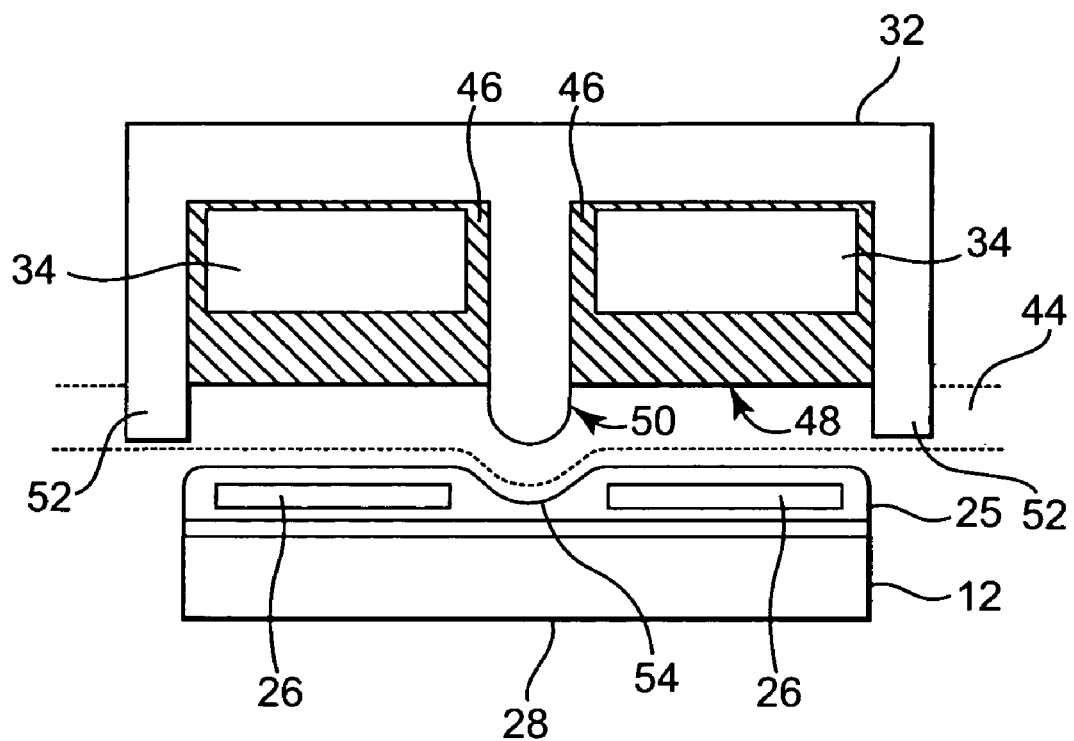
FIG. 5 is a cross-sectional illustration of an embodiment of the external antenna having peripheral protrusions and of an implantable medical device having an mating indent with a central protrusion of the external antenna.
Figure 6:
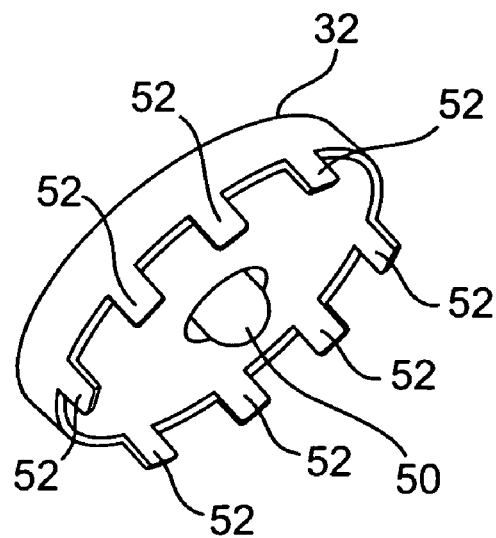
FIG. 6 is a bottom perspective view of the external antenna of FIG. 5.

An alternative embodiment of external antenna 32 of charging system 10 can be seen by referring to FIG. 5 and FIG. 6. FIG. 5 is a cross-sectional view of external antenna 32 placed in the proximity of implantable medical device 12 and secondary coil 26. FIG. 6 is an underside perspective view of external antenna 32 unencumbered by implantable medical device 12.

As in FIG. 3 and FIG. 4, external antenna 32 of FIG. 5 and FIG. 6 has central protrusion 50 enhancing electromagnetic coupling between primary coil 34 and secondary coil 26 as discussed above. In addition, external antenna 32 contains a plurality of peripheral protrusions 52 extending beyond surface 48 in a similar fashion to central protrusion 50. Peripheral protrusions 52 may be sized and positioned to "fit" around the periphery of internal antenna 25 of implantable medical device 12 to further reduce the gap between primary coil 34 and secondary coil 26. One or more peripheral protrusions 52 may be used. Peripheral protrusions may be circular in cross-section, conically shaped, square, rectangular or arcuate. Typically, peripheral protrusions 52 extend a similar distance beyond surface 48 as central protrusion 50, however, peripheral protrusions 52 may extend farther or less far from surface 48 than central protrusion 50. Peripheral protrusions 52 may extend approximately one-half of the distance that central protrusion 50 extends from surface 48.

Peripheral protrusions 52 may be spaced from one another as illustrated in FIG. 6 or may be more or less continuous around a periphery of external antenna 32 forming, to a large extent or entirely, a peripheral ring around external antenna 32 extending below surface 48.

In an embodiment illustrated in FIG. 5, implantable medical device 12, and, in particular, internal antenna 25, has an indent 54 on the surface facing cutaneous boundary 44 aligned with central protrusion 50. So configured, indent 54 of internal antenna 25 provides a locating feature allowing the user to tactilely determine the optimum positioning of external antenna 32 and will help hold external antenna 32 in proper position for electromagnetic energy transfer and will help ensure efficient energy transfer. Further, indent 54 may allow magnetic core 38 in protrusion 50 to get even closer to secondary coil 26 making energy transfer even more efficient.

In an embodiment illustrated in FIG. 5 and FIG. 6, peripheral protrusions 52 may be sized and positioned to have a pattern, perhaps a circular pattern, slightly larger in diameter than internal antenna 25 allowing peripheral protrusions 52 to "fit" over the edge of internal antenna 25 enabling ease of tactile positioning of external antenna 32 with respect to internal antenna 25. Further, peripheral protrusions 52 positioned in this manner may tend to push away skin of cutaneous boundary 44 and stretch cutaneous boundary 44 to be more thin over internal antenna 25 allowing external antenna 32 and, hence, primary coil 34, to be closer to secondary coil 26 and increasing the efficiency of energy transfer.

Figure 7:
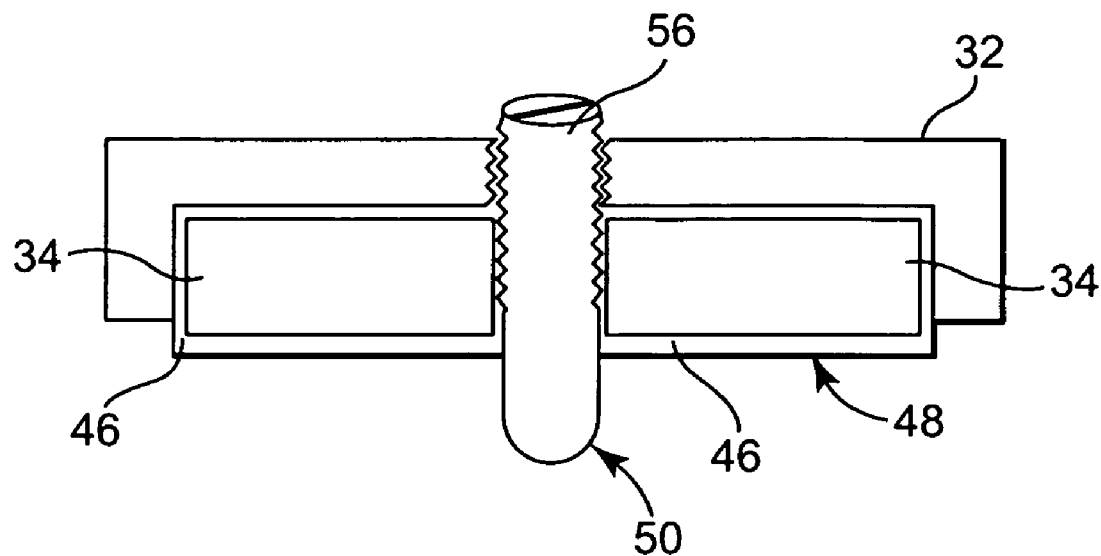
FIG. 7 is a cross-sectional illustration of an embodiment of an external antenna having an adjustable central protrusion.

FIG. 7 illustrates an embodiment of external antenna 32 having screw 56 facilitating implementation of central protrusion 50. Screw 56 may be turned clockwise or counter-clockwise to either increase the amount of protrusion or decrease the amount of protrusion of central protrusion 50 from surface 48. Screw 56 may be turned by hand or by using a tool such as a screwdriver in a slot of the top surface of screw 56. Screw 56 may extend through external antenna 32 as shown, facilitating tool manipulation, or may extend only partly through external antenna 32 allowing manipulation, for example, by hand turning central protrusion 50. Screw 56 may be adjusted to create a greater or lesser extension of central protrusion 50 to account for patient comfort, varying implant locations and implant depths and type of skin or amount of fat tissue surrounding implantable medical device 12.

Figure 8:
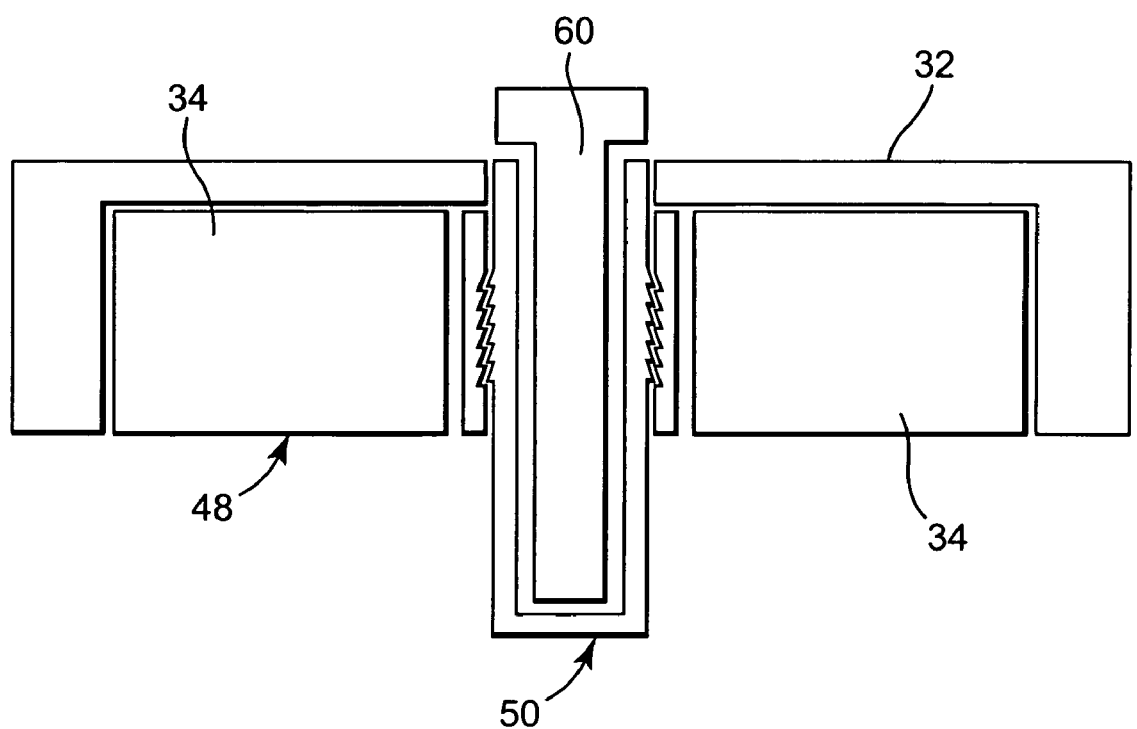
FIG. 8 is a cross-sectional illustration of an embodiment of an external antenna having a rachetable central protrusion.

FIG. 8 illustrates an embodiment of external antenna 32 similar to the embodiment illustrated in FIG. 7. However, in the embodiment illustrated in FIG. 8, adjustable central protrusion 50 is designed to an adjustable plunger that ratchets within the body of external antenna 32. The ratchet mechanism can allow central protrusion 50 to be adjusted relative to surface 48.

Figure 9:
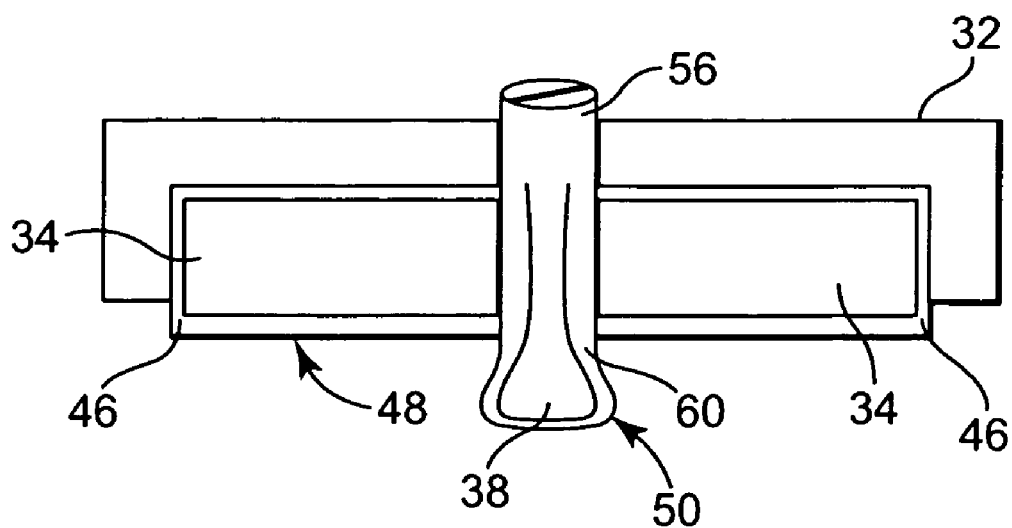
FIG. 9 is a cross-sectional illustration of an embodiment of an external antenna having a magnetic core of non-uniform cross-section.

FIG. 9 illustrates an embodiment of external antenna 32 in which magnetic core 38 has a non-uniform cross-sectional area. Screw 56 is constructed of magnetic core 38 having a larger cross-section nearer the tip of central protrusion 50 and a smaller cross-section farther away from the tip of central protrusion 50. The greater amount of magnetic core 38 nearer the tip of central protrusion 50 increases the focusing effect of magnetic core 38 and increases the efficiency of energy transfer by keeping electromagnetic flux within magnetic core 38 farther toward secondary coil 26. The remainder of screw 56 may be comprised of a non-magnetic protective material 60 such as an injection molded thermoplastic such as nylon 12, nylon PPA, polycarbonate or ABS. While the embodiment of FIG. 8 is illustrated with magnetic core 38 contained within screw 56, it is to be recognized and understood that magnetic core 38 could also be contained within external antenna 32 and within central protrusion 50 without an adjustable screw 56. That is, central protrusion 50 could be fixed and still contain magnetic core 38 on non-uniform cross-section.

While various embodiments of central protrusion 50 have been described, it is to be recognized and understood such embodiments and techniques could be used for one or more of peripheral protrusions 52, either in addition to be used with central protrusion 50 or alternative to being used with central protrusion 50.

While peripheral protrusions 52 have been illustrated and described as being used with central protrusion 50, it is to be recognized and understood that peripheral protrusions 52 could be used to benefit in external antenna 32 without central protrusion 50.

In an embodiment, a portion of insulating material 46 facing surface 48 could be formed of a low permeable material, such as bismuth graphite, to assist in forcing the electromagnetic field generated by primary coil 34 toward secondary coil 26.

Thus, embodiments of the invention are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An antenna for a completely external power source for an implantable medical device situated completely under a continuous cutaneous boundary of a patient, said implantable medical device having therapeutic componentry and a secondary coil operatively coupled to said therapeutic componentry, comprising:
   a housing having a first surface adapted to be placed closest to said secondary coil of said implantable medical device; and
   a primary coil operatively coupled to said external power source and inductively energizing said secondary coil transcutaneously across said continuous cutaneous boundary, said primary coil being wound forming generally concentric loops having an axis;
   said housing having a central protrusion centrally located with respect to said axis of said primary coil extending from said first surface, a peripheral protrusion extending from said first surface at least partially surrounding an outer periphery of said primary coil, and an area between said central protrusion and said peripheral protrusion co-planar with said first surface.

2. The antenna of claim 1 wherein said central protrusion comprises a magnetic core.

3. The antenna of claim 1 further comprising a magnetic core at least partially contained in said central protrusion.

4. The antenna of claim 1 wherein said peripheral protrusion comprises a plurality of bumps, spaced from each other, surrounding said outer periphery of said primary coil and extending from said first surface.

5. The antenna of claim 1 wherein said peripheral protrusion extends from said first surface approximately one-half centimeter.

6. The antenna of claim 1 wherein said peripheral protrusion extends from said first surface not greater than said central protrusion extends from said first surface.

7. The antenna of claim 6 wherein said peripheral protrusion extends from said first surface less than said central protrusion extends from said first surface.

8. The antenna of claim 6 wherein said peripheral protrusion extends from said first surface approximately one-half of the distance said central protrusion extends from said first surface.

9. The antenna of claim 1 wherein said central protrusion is generally aligned with said axis of said primary coil.

10. The antenna of claim 9 wherein said central protrusion has a circular cross-section.

11. The antenna of claim 10 wherein said central protrusion has a round tip.

12. The antenna of claim 10 wherein said central protrusion is conical.

13. The antenna of claim 9 wherein a diameter of said circular cross-section of said central protrusion is not greater than a distance between an inner periphery of said primary coil.

14. The antenna of claim 1 wherein said central protrusion extends from said first surface approximately one-half centimeter.

15. An antenna for a completely external power source for an implantable medical device situated completely under a continuous cutaneous boundary of a patient, said implantable medical device having therapeutic componentry and a secondary coil operatively coupled to said therapeutic componentry, comprising:

a housing having a first surface adapted to be placed closest to said secondary coil of said implantable medical device; and a primary coil operatively coupled to said external power source and inductively energizing said secondary coil transcutaneously across said continuous cutaneous boundary, said primary coil being wound forming generally concentric loops having an axis;

said housing having a protrusion extending from said first surface;

wherein an extent of extension of said protrusion from said first surface is adjustable.

16. The antenna of claim 15 wherein said protrusion comprises a screw having threads adapted to mate with corresponding threads of said housing.

17. The antenna of claim 15 wherein said protrusion comprises a ratchet plunger having mating teeth features to mate with corresponding teeth of said housing.

18. A system for transcutaneous energy transfer across a continuous cutaneous boundary, comprising:

a completely implantable medical device, comprising:
a therapeutic componentry; and
a secondary coil operatively coupled to said therapeutic componentry; and a completely external power source, comprising:
an antenna comprising:
a housing having a first surface adapted to be placed closest to said secondary coil of said implantable medical device; and
a primary coil operatively coupled to said external power source and inductively energizing said secondary coil transcutaneously across said continuous cutaneous boundary when externally placed in proximity of said secondary coil, said primary coil being wound forming generally concentric loops having an axis;
said housing having a central protrusion centrally located with respect to said axis of said primary coil extending from said first surface, a peripheral protrusion extending from said first surface at least partially surrounding an outer periphery of said primary coil, and an area between said central protrusion and said peripheral protrusion co-planar with said first surface.

19. A method of transcutaneous energy transfer across a continuous cutaneous boundary to a medical device completely implanted in a patient having a secondary charging coil using an external power source having a housing containing a primary coil, said housing having a first surface nearest to said secondary coil, said housing having a protrusion extending from said first surface, comprising the steps of:

positioning said primary coil completely externally of said patient with respect to said secondary coil;

pressing said protrusion and said first surface against skin of said patient;

transferring energy transcutaneously across said continuous cutaneous boundary from said primary coil to said secondary coil.

20. The method of claim 19 wherein said protrusion is a central protrusion centrally located with respect to an axis of said primary coil.

21. The method of claim 20 further comprising the step of adjusting a distance of extension of said protrusion.

22. The method of claim 20 wherein said pressing step further comprises pressing a peripheral protrusion extending from said first surface at least partially surrounding an outer periphery of said primary coil against said skin of said patient.

23. The method of claim 22 wherein said peripheral protrusion comprises a plurality of bumps, spaced from each other, surrounding said outer periphery of said primary coil and extending from said first surface.

24. The method of claim 20 wherein said housing further has a peripheral protrusion extending from said first surface at least partially surrounding an outer periphery of said primary coil and which further comprises the step of pressing said peripheral protrusion against said skin of said patient.

25. The method of claim 20 wherein said central protrusion comprises a magnetic core.

26. The method of claim 20 wherein said housing further comprises a magnetic core carried at least partially in said central protrusion.

27. The method of claim 19 wherein said pressing step displaces at least some of said cutaneous boundary.

\* \* \* \* \*